United States Patent [19]

Hamel et al.

[11] Patent Number: 4,801,461
[45] Date of Patent: * Jan. 31, 1989

[54] PSEUDOEPHEDRINE DOSAGE FORM

[75] Inventors: Larry G. Hamel, Sunnyvale; Felix A. Landrau, Milpitas; George V. Guittard, Cupertino; Patrick S. L. Wong, Hayward, all of Calif.

[73] Assignee: ALZA Corporation, Palo Alto, Calif.

[ * ] Notice: The portion of the term of this patent subsequent to May 5, 2004 has been disclaimed.

[21] Appl. No.: 7,879

[22] Filed: Jan. 28, 1987

[51] Int. Cl.4 .......................... A61K 9/24; A61K 9/44
[52] U.S. Cl. ................................... 424/467; 424/473; 424/480; 604/892.1
[58] Field of Search ............... 424/467, 473, 475, 480; 604/892.1

[56] References Cited

U.S. PATENT DOCUMENTS

| | | | |
|---|---|---|---|
| 2,799,241 | 6/1957 | Wurster | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes | 128/260 |
| 4,200,098 | 4/1980 | Ayer et al. | 128/260 |
| 4,285,987 | 8/1981 | Ayer et al. | 427/3 |
| 4,662,880 | 5/1987 | Hamel et al. | 424/473 |

*Primary Examiner*—Ellis P. Robinson
*Assistant Examiner*—Betsy Bozzelli
*Attorney, Agent, or Firm*—Paul L. Sabatine; Edward L. Mandell; Steven F. Stone

[57] ABSTRACT

A dosage form is disclosed for delivering the beneficial drug pseudoephedrine to a biological environment of use.

20 Claims, 1 Drawing Sheet

PSEUDOEPHEDRINE DOSAGE FORM

CROSS REFERENCE TO COPENDING APPLICATION

This patent application is copending with U.S. patent application Ser. No. 06/839,384 filed on March 14, 1986 now U.S. Pat. No. 4,662,880, issued May 5, 1987. This patent application and copending patent application Ser. No. 06/839,384 both are assigned to ALZA Corporation of Palo Alto, Calif.

FIELD OF THE INVENTION

This invention pertains to a dosage form comprising the beneficial drug pseudoephedrine for administering the pseudoephedrine to a recipient, and to a composition comprising the beneficial drug pseudoephedrine.

BACKGROUND OF THE INVENTION

Pseudoephedrine is a beneficial drug which occurs naturally in plants of the genus Ephedra. Pseudoephedrine is a stereoisomer and the isomeric forms include d- and l-ephedrine as well as d- and l-pseudoephedrine and racemic mixtures thereof. The drug pseudoephedrine is administered as its pharmaceutically acceptable acid addition salt. The organic and the inorganic salts used include organic salts such as ascorbate, bitartrate, citrate, fumarate, malicate, maleicate, succinate, tartrate and the like, and inorganic salts such as the hydrochloride, nitrate, phosphate, sulfate and the like.

Pharmacological pseudoephedrine is a sympathomimetic amine. Pseudoephedrine is used as a bronchodilator and as a peripheral vasoconstrictor. Pseudoephedrine is indicated for temporary relief of nasal congestion due to the common cold, for temporary relief of nasal congestion associated with sinusitis, for relief of cough due to minor throat irritation as may occur with the common cold or inhaled irritants, for promoting nasal drainage, for promoting sinus drainage, for its help in loosening phlegm and bronchial secretion, for helping rid the bronchial passage of mucus, for relief of hay fever, and for the relief of upper respiratory allergies. The therapeutic properties of pseudoephedrine are known to the medical arts in *Pharmaceutical Sciences*, by Remington, 17th Ed., p 890, 1985; *The Pharmaceutical Codex*, 11th Ed., p 761, 1981, and *The Extra Pharmacopoeia*, by Martindale, 28th Ed., p 27, 1982.

While pseudoephedrine enjoys wide acceptance by the medical-dispensing arts for its intended therapeutic indications, there are serious disadvantages associated with its use. For example, one disadvantage known to the prior art is that the medical-dispensing arts lack a dosage form that could sustain the administration of the medication at a known amount per unit time for a predetermined length of time, in contrast to the presently used conventional tablets and capsules that are administered every four hours and immediately releases all of its medication. Another disadvantage associated with the prior art drug is its instability to light, and it can be subjected to chemical attack by many agents that are used conventionally in pharmaceutical preparations.

In the light of the above presentation it will be appreciated by those versed in the dispensing arts to which this invention pertains that a critical need exists (1) for a dosage form that can deliver pseudoephedrine at a controlled rate to provide a dosage, therapeutic administration of pseudoephedrine for its beneficial effects over a prolonged time span; and (2) for a dosage form that can concomitantly and substantially provide shelter from light during storage, manufacture, and the like, and administer the medication essentially independent of individual chemical variations in an environment of use such as the gastrointestinal tract. It will be further appreciated by those versed in the art that such a novel and unique dosage form that can administer pseudoephedrine at a controlled rate over time, and simultaneously provide substantial protection from adverse effects, would represent an advancement in the art and it would also represent a valuable contribution to the art.

OBJECTS OF THE INVENTION

Accordingly, in view of the above presentation, it is an immediate object of this invention to provide a dosage form for delivering pseudoephedrine at a controlled rate which dosage form substantially overcomes the disadvantages associated with the prior art.

Another object of the present invention is to provide a dosage form that comprises means for administering pseudoephedrine at a controlled rate and for substantially protecting the pseudoephedrine against external unwanted effects while in the dosage form.

Another object of the present invention is to provide a dosage form that makes available by the dosage form pseudoephedrine therapy over a prolonged time span.

Another object of the invention is to provide a pharmaceutical dosage form comprising pseudoephedrine and which form makes available both immediate and sustained pseudoephedrine therapeutic activity.

Another object of the present invention is to provide a dosage form tht substantially reduces and/or substantially eliminates the unwanted influence of an environment of use and still provide controlled administration of the pseudoephedrine over time.

Another object of this invention is to provide a composition comprising pseudoephedrine that can be administered to biological receptor sites to produce that desired pharmacokinetic effects.

Another object of the present invention is to provide a dosage form that can dispense pseudoephedrine at a controlled rate for obtaining the pharmacological and the physiological benefit of the drug over time, and which dosage form thusly represents an improvement and an advancement in therapy.

Another object of the present invention is to provide a dosage form that comprises an exterior lamina composition comprising pseudoephedrine and a releasable binder that delivers the pseudoephedrine immediately for increasing the period of time pseudoephedrine is available for performing its beneficial effects, followed by prolonged release of pseudoephedrine from the interior of the dosage forms.

Another object of the present invention is to provide a dosage form adapted for administering pseudoephedrine to a warm-blooded animal from an exterior lamina comprising pseudoephedrine for delivering an initial pulse of the drug which acts in cooperation with the dosage form that follows the delivery of pseudoephedrine at a rate controlled by the dosage form.

Another object of the present invention is to provide a dosage form comprising a single compartment comprising a composition comprising a member selected from the group consisting of pseudoephedrine and its therapeutically acceptable salts, and which dosage form can administer the pseudoephedrine at a preselected prescribed ratio for providing a complete pharmaceutical regimen to a warm-blooded animal.

Another object of the invention is to provide a complete pharmaceutical regimen for a composition comprising pseudoephedrine, and which composition can be dispensed from the dosage system, the use of which requires intervention only for initiation and possibly termination of the regimen.

Another object of the present invention is to provide a dosage form that can dispense pseudoephedrine to a patient in need of a sympathomimetic amine, a bronchodilator, a peripheral vasoconstrictor, and for therapeutic relief of nasal and bronchial congestion, and for relief of bronchial asthma.

Other objects, features and advantages of the invention will be more apparent to those versed in the dispensing arts from the following detailed specification, taken in conjunction with the drawings and the accompanying claims.

BRIEF DESCRIPTION OF THE DRAWINGS

In the drawings figures, which are not drawn to scale, but are set forth to illustrate various embodiments of the invention, the drawing figures are as follows.

In the drawing figures and in the specification, like parts in related drawing figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
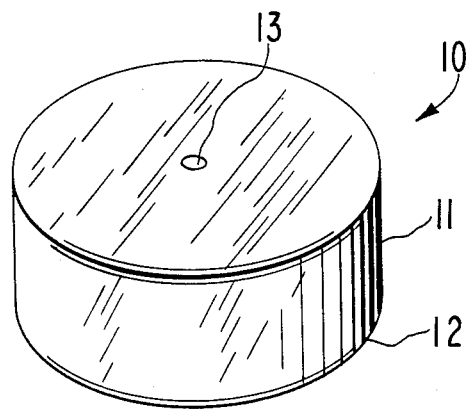
FIG. 1, is a view of a dosage form designed and shaped for orally administering the drug pseudoephedrine to the gastrointestinal tract.
Figure 2:
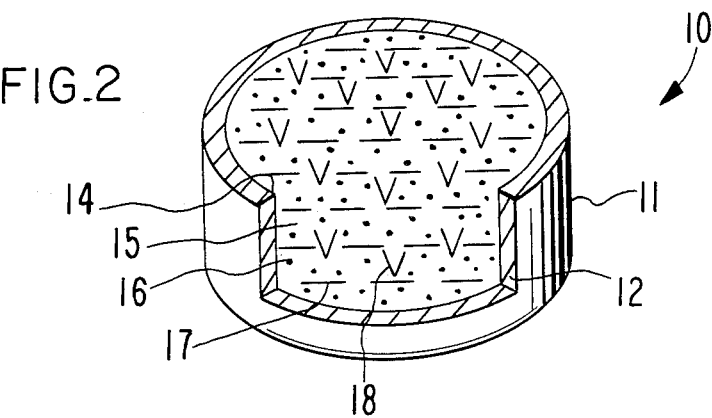
FIG. 2 is an opened view of the dosage form of FIG. 1 illustrating the internal structure of the dosage form; and, FIG. 3 is an opened view of the dosage form of FIG. 1 illustrating the structure of the dosage form and the embodiment comprising an external, immediately releasable amount of the beneficial drug pseudoephedrine.
Figure 3:
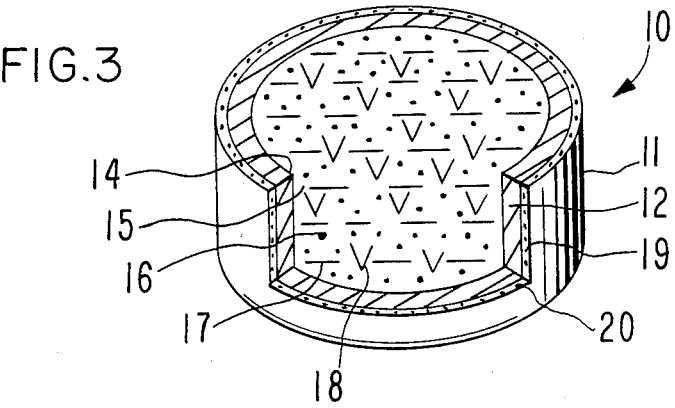

Turning now to the drawing figures in detail, which drawing figures are an example of the dosage form provided by this invention, and which example is not to be construed as limiting, one example is the dosage form illustrated in FIGS. 1, 2 and 3 and designated by the numeral 10. In FIG. 1, dosage form 10 comprises a body member 11 comprising a wall 12 that surrounds and forms an internal compartment, not seen in FIG. 1. Dosage form 10 comprises at least one exit means 13 for connecting the interior of dosage form 10 with the exterior environment of use.

In FIG. 2, dosage form 10 is seen in opened view with wall 12 sectioned at 14. In FIG. 2, dosage form 10 comprises body 11 and wall 12 that surrounds and defines an internal compartment 15. Wall 12 comprises at least one exit port 13 as seen in FIG. 1, and dosage form 10 can comprise more than one exit means.

Wall 12 of dosage form 10 comprises a composition that is permeable to the passage of an exterior fluid present in the environment of use, and it is substantially impermeable to the passage of pseudoephedrine and other ingredients present in compartment 15. The composition is semipermeable, it is substantially inert and it maintains its physical and chemical integrity during the dispensing life of the pseudoephedrine dosage form 10.

The phrase, "keeps its physical and chemical integrity" means wall 12 does not lose its structure and it does not change during the dispensing life of dosage form 10. Wall 12 comprises at least in part a composition comprising from 70 to 85 weight percent cellulose triacetate, and from 15 to 30 weight percent hydroxypropylcellulose, with the total weight percent equal to 100. Wall 12, in one presently preferred embodiment, comprises 75 weight percent cellulose triacetate and 25 weight percent hydroxypropylcellulose. In another preferred embodiment wall 12 comprises 80 weight percent cellulose triacetate and 20 weight percent hydroxycellulose. For example, the acetyl content of a cellulose triacetate can be from 35% to 43.5%. Wall 12 exhibits an increased permeability to the passage of fluid over time attributed to the presence of hydroxypropylcellulose in wall 12. The unique property of wall 12, acting in cooperation with dosage form 10, enables dosage form 10 to deliver greater than 90% to 95% of its pseudoephedrine content in a controlled manner over a prolonged period of 24 hours.

Internal compartment 15 houses a dispensable composition comprising the beneficial drug pseudoephedrine 16 identified by dots. Generally, in one osmotic dosage form provided by the invention, compartment 16 contains from 160 to 200 mg of pseudoephedrine, with more specific pseudoephedrine dosage comprising 180 mg of pseudoephedrine therapeutically acceptable acid addition salt, such as 180 mg of pseudoephedrine hydrochloride. In another dosage from provided by the invention compartment 16 contains from 80 to 115 mg of pseudoephedrine, with a more specific dosage form comprising 90 mg of pseudoephedrine therapeutically acceptable acid addition salt, such as pseudoephedrine hydrochloride. The compartment contains also an optional osmagent 17, which also functions as a solubility modifier, represented by dashes, preferably from 10 to 30 mg of osmagent, such as sodium chloride, potassium chloride and the like. The osmagent, functioning as a solubility modifier, aids in delivering a higher percentage of pseudoephedrine at a zero-order rate of delivery, usually 12 hours or longer. The compartment 16 preferably contains hydroxypropylmethylcellulose 18, generally from 2 to 9 mg, as an aid for controlling dissolution of the composition in the compartment, from 10 to 30 mg of microcrystalline cellulose, from 3 to 20 mg of polyvinylpyrrolidone, and from 0.2 to 3 mg of magnesium stearate.

In FIG. 3 dosage from 10 comprises an exterior lamina 19 coated onto the exterior surface of wall 12. Exterior lamina 19 comprises composition 20, represented by dots in lamina 19, which composition comprises pseudoephedrine as its therapeutically acceptable acid addition salt. Composition 20 also comprises an aqueous soluble releasable carrier hydroxypropylmethylcellulose. Lamina 19 comprising composition 20 provides for making available instantly pseudoephedrine, preferably as its pharmaceutically acceptable salt. In operation, when dosage form 10 is in a fluid environment of use, lamina 19 dissolves or undergoes dissolution and concurrently delivers pseudoephedrine to a drug receptor. Lamina 19 containing pseudoephedrine drug composition 20, by providing immediate pseudoephedrine delivery essentially overcomes the time required for pseudoephedrine to be delivered from compartment 15 of dosage form 10. A start-up time is needed for imbibing an external fluid, such as water, through wall 12 for dosage form 10 to hydrodynamically dispense pseudoephedrine from compartment 15 through passageway 13 to the environment of use. Lamina 19, in one presently preferred embodiment comprises 55 to 65 mg of pseudoephedrine and 5 to 20 mg of hydroxypropylmethylcellulose. In another embodiment lamina 19 comprises 25 to 35 mg of pseudoephedrine and 2 to 9 mg of hydroxypropylmethylcellulose. More specifically, in one preferred embodiment lamina 19 comprises 60 mg of pseudoephedrine and in another embodiment lamina 19 comprises 30 mg of pseudoephedrine. Lamina 19 begins to release pseudoephedrine instantly in the fluid environment of use, and it completely releases all of the pseudoephedrine during the first 30 minutes. This instant release thereby provides pseudoephedrine for immediate passage into the plasma of a recipient. Thus, a dosage form 10 provides immediate administration of pseudoephedrine followed by prolonged administration of pseudoephedrine over a prolonged time span.

The expression, "exit means" 13 as used herein comprises means and methods suitable for the metered release of beneficial drug pseudoephedrine from compartment 15 of dosage form 10. The means 13 includes at least one passageway, orifice or the like through wall 12, or through wall 12 and lamina 19 for communicating with pseudoephedrine in compartment 15. The expression, "at least one passageway" includes aperture, orifice, bore, pore, porous element through which the drug can mirgrate, hollow fiber, capillary tube, porous overlay, porous insert, and the like. The expression includes also a material that erodes or is leached from wall 12 in the fluid environment of use to produce at least one passageway in dosage form 10. Representative material suitable for forming at least one passageway, or a multiplicity of passageways, include an erodible poly(glycolic) or poly(lactic) acid member in the wall, a gelatinous filament, poly(vinyl alcohol), leachable materials such as fluid removable pore forming polysaccharides, salts, or oxides and the like. A passageway, or a plurality of passageways can be formed by leaching a material such as sorbitol from the wall. The passageway can have any shape such as round, triangular, square, elliptical, and the like, for assisting in the metered release of pseudoephedrine from dosage form 10. Dosage form 10 can be constructed with one or more passageways in spaced part relations or more than a single surface of a dosage form. Passageway and equipment for forming passageways are disclosed in U.S. Pat. Nos. 3,845,770; 3,916,899; 4,063,064 and 4,088,864. Passageways formed by leaching are disclosed in U.S. Pat. Nos. 4,200,098 and 4,285,987.

Dosage form 10 of this invention is manufactured by standard manufacturing techniques. For example, in one manufactured the compartment 15 comprising the compartment formulation ingredients are formulated by the wet granulation technique using an organic cosolvent such as isopropyl alcohol-methylene dichloride, 80/20 v/v (volume/volume), as the granulating fluid. In one manufacture the ingredients forming the compartment comprise pseudoephedrine hydrochloride, sodium chloride, hydroxypropylmethylcellulose and microcrystalline cellulose are individually passed through a 40 mesh screen and then thoroughly blended in a mixer. Next poly(vinylpyrrolidone) is dissolved in a portion of the granulation fluid, the cosolvent described immediately above. Then, the poly(vinylpyrrolidone) solution is slowly added to the dry powder blend with continual mixing in the blender. The granulating fluid is added until a wet blend is achieved, generally about 400 cc of granulating fluid per kilogram of blend. The wet mass blend is then forced through a 20 mesh screen onto over trays and dried for 18 to 24 hours at 50° C. The dried granules are then sized with a 20 mesh screen. Next magnesium stearate and, optionally, silicon dioxide are added to the dry, screened granular blend and this blend passed through an 80 mesh screen. The granulation then is placed into a V-blender for 10 to 15 minutes.

In a presently preferred process the drug pseudoephedrine and other ingredients are blended in an aqueous fluid bed granulation. In this process the drug and the ingredients forming compartment 15, that is, pseudoephedrine hydrochloride, osmagent sodium chloride, hydroxypropylmethylcellulose, microcrystalline cellulose and poly(vinylpyrrolidone) are dry blended in a fluid granulator. Next, poly(vinylpyrrolidone) dissolved in an aqueous granulation fluid is slowly sprayed onto the dry powder blend with continual mixing in the granulator. Next, the granules are dried in the granulator. Then, magnesium stearate and, optionally, silicon dioxide are added to the dry granular blend.

In either of the above processes the composition forming blend is then tabletted using a high speed tablet press. Two dosage forms are tabletted using the press, one using a 9/32 inch (7.15 mm) round, standard concave punch, and the other using a ⅜ inch (9.52 mm) round, standard concave punch.

The wall 12 of the dosage form and the exterior instant release lamina can be formed in one technique using the air suspension procedure. This procedure consists in suspending and tumbling the pseudoephedrine pressed compartment forming core in a current of air and a wall forming composition, or a lamina forming composition until--in either operation--the wall or the lamina is applied to the drug forming compartment. The air suspension procedure is well suited for independently forming the wall or the lamina. The air suspension procedure is described in U.S. Pat. No. 2,799,241; in J. Am. Pharm. Assoc., Vol. 48, pp 451 to 459, 1959; and ibid Vol. 49, pp 82 to 84, 1960. Dosage forming systems also can be coated with the wall forming composition with a Wurster ® air suspension coater using methylene dichloride/methanol cosolvent, 80/20 wt/wt, using 2.5 to 4% solids. The Aeromatic ® air suspension coater using a methylene dichloride/methanol cosolvent, 87/13 wt/wt, also can be used for applying the wall or the lamina. Other wall and laminating techniques such as pan coating can be used for manufacturing the dosage form. In the pan coating system wall forming or lamina forming compositions are deposited by successive spraying of the compositions on the drug accompanied by tumbling in a rotating pan. A pan coater is used to produce a thicker wall or lamina. A larger volume of methanol can be used in a cosolvent to produce a thinner wall or a lamina. Finally, the wall or lamina coated cmpartments are dried in a forced air over at 50° C. for a one to seven days to free the dosage form of solvent. Generally the wall formed by these techniques will have a thickness of 2 to 20 mils with a presently preferred thickness of 4 to 10 mils. The exterior lamina generally will have a thickness of 0.3 to 8 mils.

Exemplary solvents suitable for manufacturing the wall or the lamina include inert inorganic and organic solvents that do not adversely harm the wall, the lamina and the final dosage form. The solvents broadly include a member selected from the group consisting of alcohols, ketone, esters, ethers, aliphatic hydrocarbons, halogenated solvents, cycloaliphatic solvents, aromatic, heterocyclic, aqueous solvents, and mixtures thereof.

Following the procedures of this invention a number of dosage forms were prepared for administering pseudoephedrine. Representative dosage forms comprise (1) a total of 240 mg of pseudoephedrine with the drug distributed in the dosage form comprising 180 mg of pseudoephedrine in the compartment and 60 mg of pseudoephedrine in the lamina; (2) a total of 210 mg in the dosage form with the pseudoephedrine distribution comprising 90 mg of pseudoephedrine in the compartment and 30 mg of pseudoephedrine in the lamina; and (3) 90 mg of pseudoephedrine in the compartment and 30 mg of pseudoephedrine in the lamina.

A representative example of a dosage form is as follows: a compartment comprising 180 mg of pseudoephedrine, 23.4 mg of sodium chloride, 7.4 mg of hydroxypropylmethylcellulose, 24.7 mg of microcrystalline cellulose, 9.9 to 15 mg of poly(vinylpyrrolidone) and 0.6 to 2.6 mg of magnesium stearate, a wall comprising 75% cellulose acetate having an acetyl content of 43.5% and 25% hydroxypropylcellulose, and a lamina comprising 60 mg of pseudoephedrine and 7.5 to 16.5 mg of hydroxymethylcellulose. The dosage form can comprise an additional outermost coat of hydroxypropylmethylcellulose to mask its taste and to improve its appearance. The dosage form has at least one 0.5 mm passageway and more preferably four 0.5 mm passageways, and delivers its compartment pseudoephedrine hydrochloride in solution at the metered-release-rate of approximately 10 mg/hr.

Another representative dosage form comprising a total of 120 mg of pseudoephedrine is as follows: a compartment comprising 90 mg of pseudoephedrine, 11.7 mg of sodium chloride, 3.7 mg of hydroxypropylmethylcellulose, 12.4 mg of microcrystalline cellulose, 4.9 to 7.5 mg of poly(vinylpyrrolidone) and 0.3 to 1.3 mg of magnesium stearate, a wall comprising 75% cellulose triacetate having an acetyl content of 43.5% and 25% hydroxypropylcellulose and an exterior lamina on the exterior surface of the inside wall comprising 30 mg of pseudoephedrine and 3.7 to 8.3 mg of hydroxypropylmethylcellulose. The dosage form has two 0.5 mm passageways and dispenses the pseudoephedrine hydrochloride in solution at a metered rate of about 5 mg/hr over a period of 12 hours.

In summary, it will be appreciated that the present invention contributes to the art an unobvious dosage form that possesses practical utility, can administer pseudoephedrine instantly and at a dose metered-release-rate per unit time, and provide an opaque semipermeable wall for lessening unwanted environmental effects on the pseudoephedrine wall in the dosage form. While the invention has been described and pointed out in detail with reference to operative embodiments thereof, it will be understood that those skilled in the art will appreciate that various changes, modifications, substitutions and omissions can be made without departing from the spirit of the invention. It is intended, therefore, that the invention embrace those equivalent within the scope of the claims which follows.

We claim:

1. A dosage form for delivering the beneficial drug pseudoephedrine to an environment of use, the dosage form comprising:
    (a) a compartment
    (b) a dosage amount of about 160 to 200 mg of a member selected from the group consisting of pseudoephedrine and its therapeutically acceptable salts in the compartment;
    (c) a wall comprising at least in part from 70 to 85 weight percent of a cellulose acetate comprising an acetyl content of 35% to 43.5% and from 15 to 30 weight percent hydroxypropylcellulose, which wall is permeable to the passage of an external fluid, surrounds and defines the compartment and aids in protecting pseudoephedrine present in the compartment from a premature exposure to the environment of use;
    (d) at least one passageway in the wall for connecting the compartment with the exterior of the dosage form;
    (e) a lamina comprising 55 to 65 mg of a member selected from the group consisting of pseudoephedrine and its therapeutically acceptable salts in laminar arrangement with the exterior of the wall; and,
    (f) wherein, when the dosage form is in operation, the dosage form administers the pseudoephedrine immediately from the lamina and at a metered release rate per unit time from the compartment.

2. The dosage form for delivering the beneficial pseudoephedrine according to claim 1, wherein the pseudoephedrine is pseudoephedrine hydrochlorde.

3. The dosage form for delivering the beneficial pseudoephedrine according to claim 1, wherein the compartment comprises 10 to 30 mg of a pharmaceutically acceptable osmagent.

4. The dosage form for delivering the beneficial pseudoephedrine according to claim 1, wherein the compartment comprises 180 mg of pseudoephedrine.

5. The dosage form for delivering the beneficial pseudoephedrine according to claim 1, wherein the compartment comprises 2 to 9 mg of hydroxypropylmethycellulose.

6. The dosage for delivering the beneficial pseudoephedrine according to claim 1, wherein the compartment comprises 10 to 30 mg of microcrystalline cellulose.

7. A dosage form for delivering the beneficial drug pseudoephedrine to an environment of use, the dosage form comprising:
    (a) a compartment;
    (b) a dosage amount of about 80 to 115 mg of a member selected from the group consisting of pseudoephedrine and its therapeutically acceptable salts in the compartment;
    (c) a wall comprising at least in part from 70 to 85 weight percent of a cellulose acetate comprising an acetyl content of 35% to 43.5% and from 15 to 30 weight percent hydroxypropylcellulose, which wall permeable to the passage of an external fluid, surrounds and defines the compartment and aids in sheltering pseudoephedrine in the compartment from a premature exposure to the environment of use;
    (d) at least one passageway in the wall for connecting the compartment with the exterior of the dosage form;
    (e) a lamina comprising from 25 to 35 mg of a member selected from the group consisting of pseudoephedrine and its therapeutically acceptable addition salts in laminar arrangement with the exterior of the wall; and,
    (f) wherein, when the dosage form is in operation, the dosage form administers the pseudoephedrine immediately from the lamina and at a metered release rate per unit time from the compartment.

8. The dosage form for delivering the beneficial pseudoephedrine according to claim 7, wherein the pseudoephedrine is pseudoephedrine hydrochloride.

9. The dosage form for delivering the beneficial pseudoephedrine according to claim 7, wherein the compartment comprises 10 to 30 mg of a pharmaceutically acceptable osmagent.

10. The dosage form for delivering the beneficial pseudoephedrine according to claim 7, wherein the compartment comprises 2 to 9 mg of hydroxypropylmethylcellulose.

11. The dosage form for delivering the beneficial pseudoephedrine according to claim 7, wherein the compartment comprises 10 to 30 mg of microcrystalline cellulose.

12. A dosage form for delivering the beneficial drug pseudoephedrine to a warm-blooded animal, wherein the dosage form comprises: a wall comprising a member selected from the group consisting of cellulose acetate and cellulose triacetate for imparting physical and chemical integrity to the wall, and hydroxypropylcellulose, which wall surrounds a compartment; at least one passageway in the wall communicating with the compartment and the exterior of the dosage form; and, a therapeutic composition in the compartment comprising about 180 mg of pseudoephedrine hydrochloride, about 23 mg of sodium chloride and about 7.5 mg of hydroxypropylmethylcellulose.

13. The dosage form for delivering the beneficial drug pseudoephedrine to a warm-blooded animal according to claim 12, wherein the composition comprises poly(vinylpyrrolidone) and magnesium stearate.

14. The dosage form for delivering the beneficial drug pseudoephedrine to a warm-blooded animal according to claim 12, wherein the dosage form comprises a lamina comprising 60 mg of pseudoephedrine hydrochloride on the exterior surface of the wall.

15. A dosage form for delivering the beneficial drug pseudoephedrine to a warm-blooded animal, wherein the dosage form comprises: a wall comprising a member selected from the group consisting of cellulose acetate and cellulose triacetate for maintaining the physical and chemical integrity of the wall and hydroxypropylcellulose that surrounds a compartment; at least one passageway in the wall that communicates the compartment with the exterior of the dosage form; and, a therapeutic composition in the compartment comprising about 90 mg of pseudoephedrine hydrochloride, about 11.7 mg of sodium chloride and about 3.7 mg of hydroxypropylmethylcellulose.

16. The dosage form for delivering the beneficial drug pseudoephedrine to a warm-blooded animal according to claim 15, wherein the composition comprises poly(vinylpyrrolidone) and magnesium stearate.

17. The dosage form for delivering the beneficial drug pseudoephedrine to a warm-blooded animal according to claim 15, wherein the dosage form comprises a lamina comprising about 30 mg of pseudoephedrine hydrochloride on the exterior surface of the wall.

18. The dosage form for delivering the beneficial drug pseudoephedrine to a warm-blooded animal according to claim 15, wherein the passageway is a pore.

19. The dosage form for delivering the beneficial pseudoephedrine according to claim 1, wherein the cellulose acetate is cellulose triacetate.

20. The dosage form for delivering the beneficial pseudoephedrine according to claim 7, wherein the cellulose acetate is cellulose triacetate.

* * * * *